(12) United States Patent
Miyauchi et al.

(10) Patent No.: US 7,374,674 B2
(45) Date of Patent: May 20, 2008

(54) LIQUID CHROMATOGRAPHY APPARATUS

(75) Inventors: Hirotoshi Miyauchi, Yokohama (JP); Gen-ichi Uematsu, Sagamihara (JP)

(73) Assignee: Tosoh Corporation, Shunan-shi (JP)

( * ) Notice: Subject to any disclaimer, the term of this patent is extended or adjusted under 35 U.S.C. 154(b) by 557 days.

(21) Appl. No.: 10/934,399

(22) Filed: Sep. 7, 2004

(65) Prior Publication Data
US 2005/0051468 A1   Mar. 10, 2005

(30) Foreign Application Priority Data
Sep. 9, 2003 (JP) ............................. 2003-317401

(51) Int. Cl.
*B01D 15/08* (2006.01)
(52) U.S. Cl. .................... 210/198.2; 210/175; 210/232
(58) Field of Classification Search ................ 210/635, 210/656, 659, 143, 96.1, 175, 181, 198.2, 210/232
See application file for complete search history.

(56) References Cited

U.S. PATENT DOCUMENTS

| | | | |
|---|---|---|---|
| 3,429,176 A | 2/1969 | Topham | |
| 5,135,549 A * | 8/1992 | Phillips et al. .................... 95/8 |
| 5,196,039 A * | 3/1993 | Phillips et al. ............... 210/656 |
| 5,340,543 A | 8/1994 | Annino et al. | |
| 6,170,267 B1 | 1/2001 | Kitaoka | |
| 6,248,158 B1 * | 6/2001 | Abdel-Rahman et al. ..... 96/101 |
| 6,303,029 B1 * | 10/2001 | Nurok et al. ............ 210/198.3 |
| 6,311,544 B1 * | 11/2001 | Bertrand .................... 73/23.35 |
| 2002/0178786 A1 | 12/2002 | White et al. | |

FOREIGN PATENT DOCUMENTS

| | | |
|---|---|---|
| DE | 100 17 351 A1 | 10/2001 |
| EP | 0 499 445 A2 | 8/1992 |
| JP | 3008595 | 12/1999 |
| JP | 2001-74721 | 3/2001 |

* cited by examiner

*Primary Examiner*—Ernest G. Therkorn
(74) *Attorney, Agent, or Firm*—Oblon, Spivak, McClelland, Maier & Neustadt, P.C.

(57) ABSTRACT

A liquid chromatography apparatus includes a separation column, liquid feed pump which feeds eluent into the separation column, a detector which detects elution component fed from the separation column, and a plurality of valves which control a flow of liquid which passes from the liquid feed pump to the detector via the separation column, wherein the liquid feed pump, the separation column, the detector, and the plurality of valves are disposed in a cooled portion within a first unit, and among the mechanical parts and the electrical parts that respectively form the liquid feed pump, the detector, and the plurality of valves, the electrical parts are disposed in a non-cooled portion within the first unit.

14 Claims, 7 Drawing Sheets

LIQUID CHROMATOGRAPHY APPARATUS

BACKGROUND OF THE INVENTION

1. Field of the Invention

The present invention relates to a liquid chromatography apparatus, and in particular, relates to a cooling system of the liquid chromatography apparatus.

Priority is claimed on Japanese Patent Application No. 2003-317401, filed Sep. 9, 2003, the contents of which are incorporated herein by reference.

2. Description of Related Art

In the case in which a separation of a thermally unstable substance, such as a biopolymer, is performed using a liquid chromatography apparatus, the procedure was conventionally performed by placing the entire liquid chromatography apparatus into a refrigerated room, a refrigerated case, or the like.

Japanese Unexamined Patent Application, First Publication No. 2001-74721 (Patent Document 1) discloses a liquid chromatography apparatus in which the temperature adjustments of an eluent supply unit, a liquid feed pump, an injection valve, and a column holding portion are performed by a heated air. Japanese Patent No. 3008595 (Patent Document 2) solved a problem that a warmed sample forms a deposit after injection, by maintaining a sample dissolution tank and a separating column at constant temperature. Although each of these patent documents discloses the technology of performing temperature adjustment of a part of a liquid chromatography apparatus, they do not address the case of the separation of a thermally unstable substance, such as a biopolymer, which must be performed under low-temperature conditions.

By using the conventional method of placing an entire liquid chromatography apparatus into the refrigerated room and the like, the system for holding the liquid chromatography apparatus must be large, and the workability of placing the liquid chromatography apparatus has also been inferior as a worker must frequently walk in and out of the refrigerated room and the like. Furthermore, because the entire liquid chromatography apparatus is refrigerated, failure of the electrical system may occur frequently by condensation and the like.

SUMMARY OF THE INVENTION

In consideration of the above described problems, an object of the present invention is to provide a liquid chromatography apparatus in which a failure of an electrical system is not likely to occur, a worker is able to perform simple operations, the composition thereof is compact and the separation of a thermally unstable substance, such as biopolymer, can be performed.

A liquid chromatography apparatus according to the present invention provides a separation column, a liquid feed pump which feeds eluent into the separation column, a detector which detects elution component fed from the separation column, and a plurality of valves which control a flow of liquid which passes from the liquid feed pump to the detector via the separation column, wherein the liquid feed pump, the separation column, the detector, and the plurality of valves are disposed in a cooled portion within a first unit, and among the mechanical parts and the electrical parts that respectively form the liquid feed pump, the detector, and the plurality of valves, the electrical parts are disposed in a non-cooled portion within the first unit. According to such a composition, in the case in which the sample is fed to each of the above-mentioned apparatus, it is possible for the portion with which the sample is in contact to be cooled.

Moreover, a liquid chromatography apparatus according to the present invention provides a separation column, a liquid feed pump which feeds eluent into the separation column, a detector which detects elution component fed from the separation column, and a plurality of valves which control a flow of liquid which passes from the liquid feed pump to the detector via the separation column, wherein at least one part of each of the liquid feed pump, the detector and the plurality of valves, as well as the separation column are disposed in a cooled portion formed at the inside of a first unit, and at least one of parts which require supply of electricity of the liquid feed pump, the detector and the plurality of valves is disposed in a non-cooled portion formed at the inside of the first unit. According to such a composition, in the case in which the sample is fed to each of the above-mentioned apparatus, it is possible for the portion which the sample touches to be cooled.

Here, another part which requires supply of electricity is also called electrical parts. The electrical parts are parts which require supply of electricity such as an electrical circuit, a substrate, a power supply, a motor, a connector, and the like. Mechanical parts mean parts other than the electrical parts.

Moreover, among the detector which consists of a light source, a lens, a cell, and a light receiving portion, the light source, the lens and the light receiving portion are included in the electrical parts, and only the cell is included in the mechanical parts.

In the present invention, it is not necessary for all of parts which require supply of electricity (electrical parts) to be disposed in the non-cooled portion, and it is possible for only one of parts which require supply of electricity to be disposed in the non-cooled portion. Moreover, in the present inventions it is not necessary for all of mechanical parts to be disposed in the cooled portion, and it is possible for only one of mechanical parts to be disposed in the cooled portion.

Furthermore, in the detector, in the case that the optical system up to the light receiving portion is disposed adjacent to the cell due to detector design considerations or with the object of improving the detector sensitivity, all or a part of these can be included in the mechanical parts and disposed in the cooled portion. For example, in the case of a configuration in which the light source and the cell are connected by an optical fiber, a lens disposed at the cell side end of the optical fiber in order to make the emitted light parallel light and the light receiving portion that receives the light that transits the cell are disposed adjacent to the cell within the cooled portion as mechanical parts, and thereby, it is possible to present an example of a configuration in which the detector sensitivity is improved while satisfying the design constraints of the detector. Note that in the case that the cell is, for example, a flow cell, the lenses may be incorporated into the opening at which the light is incident to the cell and the opening at which the light is emitted from the cell. However, in this case, these lenses integrally formed with the cell, and thus they are included in the mechanical parts.

In the present invention, by insulating the electrical parts thermally from the cold, condensation on the electrical parts can be prevented, and thereby, a liquid chromatography apparatus in which failure of the electrical system is not likely to occur can be obtained. In addition, by insulating the electrical parts thermally from the cold, it is possible for the heat generated from the electrical parts not to be transmitted to the cooled portion.

Note that if a fan or the like is provided in the non-cooled portion and waste heat discharged from the electrical parts such as the motor disposed in the non-cooled portion is circulated, the possibility of condensation on the electrical parts can be further reduced.

Moreover, in the liquid chromatography apparatus according to the present invention, the liquid feed pump and the plurality of valves may be arranged on an attached panel fitted in the cooled portion at the inside of the first unit.

In the present invention, by arranging the liquid feed pump and the plurality of valves on the attached panel, the liquid chromatography apparatus in which the worker is able to perform operations simply and the composition thereof is compact can be obtained.

Moreover, in the liquid chromatography apparatus according to the present invention, regarding the attached panel, it is desirable that at least one part of an area where the liquid feed pump and the plurality of valves are arranged be inclined.

In the present invention, by inclining at least one part of an area where the liquid feed pump and the plurality of valves are arranged, the area of the attached panel can be extended in a limited space that is in the cooled portion at the inside of the first unit. In addition, by inclining the surface of the attached panel, there is also an advantage that cold air easily flows around each apparatus arranged at an inclined portion.

Moreover, by such an inclining, it is also advantageous that the maintenance such as replacement, repair, or the like of each apparatus installed on the inclined portion becomes easy.

Furthermore, the liquid chromatography apparatus according to the present invention includes a first unit which has an opening portion on the side to pass through the cold air, a second unit which has an opening portion on the side to allow the cold air to pass through, and divides the inside thereof into upper and lower portions to preserve the sample, and a cooling apparatus, wherein the first unit, the second unit, and the cooling apparatus may be attached to or removed from each other.

In the present invention, by unitizing the first unit, the second unit to preserve the sample, and the cooling apparatus, respectively, and being able to be attached to or removed from each other, an optimal combination of the apparatus can be chosen for each experiment.

Moreover, the liquid chromatography apparatus according to the present invention may be provided with a cold air route in which the cold air which flows out from a cold air flow out opening formed in the cooling apparatus flows through the inside of the second unit and returns to a cold air return opening formed in the cooling apparatus, via the cooled portion of the inside of the first unit and cold air ducts provided at the first unit and the second unit.

In the present invention, for example, by forming the cold air flow out opening of the cooling apparatus in the upper portion of the second unit, a sample put on the upper portion in the second unit can be maintained at a low temperature, while by not entering the cold air in the lower portion of the second unit, evaporation of the fractionated solution put on the lower portion in the second unit can be prevented.

Moreover, conversely, by forming the cold air flow out opening of the cooling apparatus in the lower portion of the second unit, the sample put on the lower portion in the second unit can always be maintained at a low temperature, while by not entering the cold air to the upper portion in the second unit, evaporation of the fractionated solution put on the upper portion in the second unit can be prevented.

Moreover, in the liquid chromatography apparatus according to the present invention, packings may be provided at the circumferences of the opening portions which are formed at the first unit and the second unit to allow the cold air to pass through. In the present invention, airtightness can be maintained by providing packing at the circumference of the opening portions.

Moreover, in the liquid chromatography apparatus according to the present invention, in the cold air duct provided at the first unit, a deaeration chamber for removing dissolved gas in the eluent and/or the sample may be provided.

In the present invention, by providing the deaeration chamber among a deaeration apparatus comprising of the deaeration chamber and a decompression pump in the cold air duct, the eluent and/or the sample can be cooled using surplus cold energy.

Moreover, in the liquid chromatography apparatus according to the present invention, in the cold air duct provided at the second unit, a heat sink for cooling the inside of the second unit may be provided.

In the present invention, in the case in which the cold air cannot be entered for preventing the evaporation of the fractionated solution put in the second unit, by providing the heat sink in the cold air duct of the second unit, the fractionated solution can be cooled through the heat sink.

In the liquid chromatography apparatus according to the present invention, first doors of a hollow structure may be provided at the first unit and the second unit, respectively.

Moreover, in the liquid chromatography apparatus according to the present invention, first doors of a hollow structure may be provided at the first unit and the second unit, respectively, and a check valve for preventing outside air from flowing into the hollow structure of the first door may be provided at the first door.

In the present invention, heat insulation properties of the door can be improved by making the first door be a hollow structure.

Furthermore, in the present invention, by providing the check valve at the first door, the hollow portion of the first door can be maintained at a lower pressure than the outside air to improve the heat insulation.

Although not especially limited as the material of the first door, a constitution of a transparent material of such as an acrylic resin and the like is desirable as the material of the first door so that the situation of each above-mentioned apparatus can be observed from the exterior.

Moreover, in the liquid chromatography apparatus according to the present invention, a rib for reinforcing the hollow portion of the first door may be arranged on one face plate constituting the hollow portion, and a gap may be formed between the rib and another face plate.

In the present invention, by reinforcing the hollow portion of the first door using the rib, the first door can be prevented from being deformed by atmospheric pressure.

In addition, by forming the gap between the rib and another face plate, the rib can be prevented from becoming a heat bridge.

Moreover, in the liquid chromatography apparatus according to the present invention, drying agents may be enclosed in the hollow portion of the first door.

In the present invention, because the drying agents are enclosed in the hollow portion of the first door, condensation in the hollow portion can be prevented.

Moreover, in the liquid chromatography apparatus according to the present invention, at the inside of the first door provided at the second unit, second doors to maintain the coolness may be provided in an upper portion and a lower portion of the second unit, respectively.

In the present invention, in the case in which the operation was done in the upper portion of the second unit, the coolness in the lower portion of the second unit can be maintained because the second door is provided in the lower portion of the second unit.

In contrast, in the case in which the operation was done in the lower portion of the second unit, the coolness in the upper portion of the second unit can be maintained because the second door is provided in the upper portion of the second unit.

According to the present invention, a liquid chromatography apparatus can be obtained in which failure of the electrical system is not likely to occur, a worker is able to perform operations simply, the structure thereof is compact, and a separation of the very thermally unstable substance such as a biopolymer can be performed.

DETAILED DESCRIPTION OF THE INVENTION

Hereafter, an embodiment of the liquid chromatography apparatus according to the present invention will be explained while referring to the figures.

Figure 1:
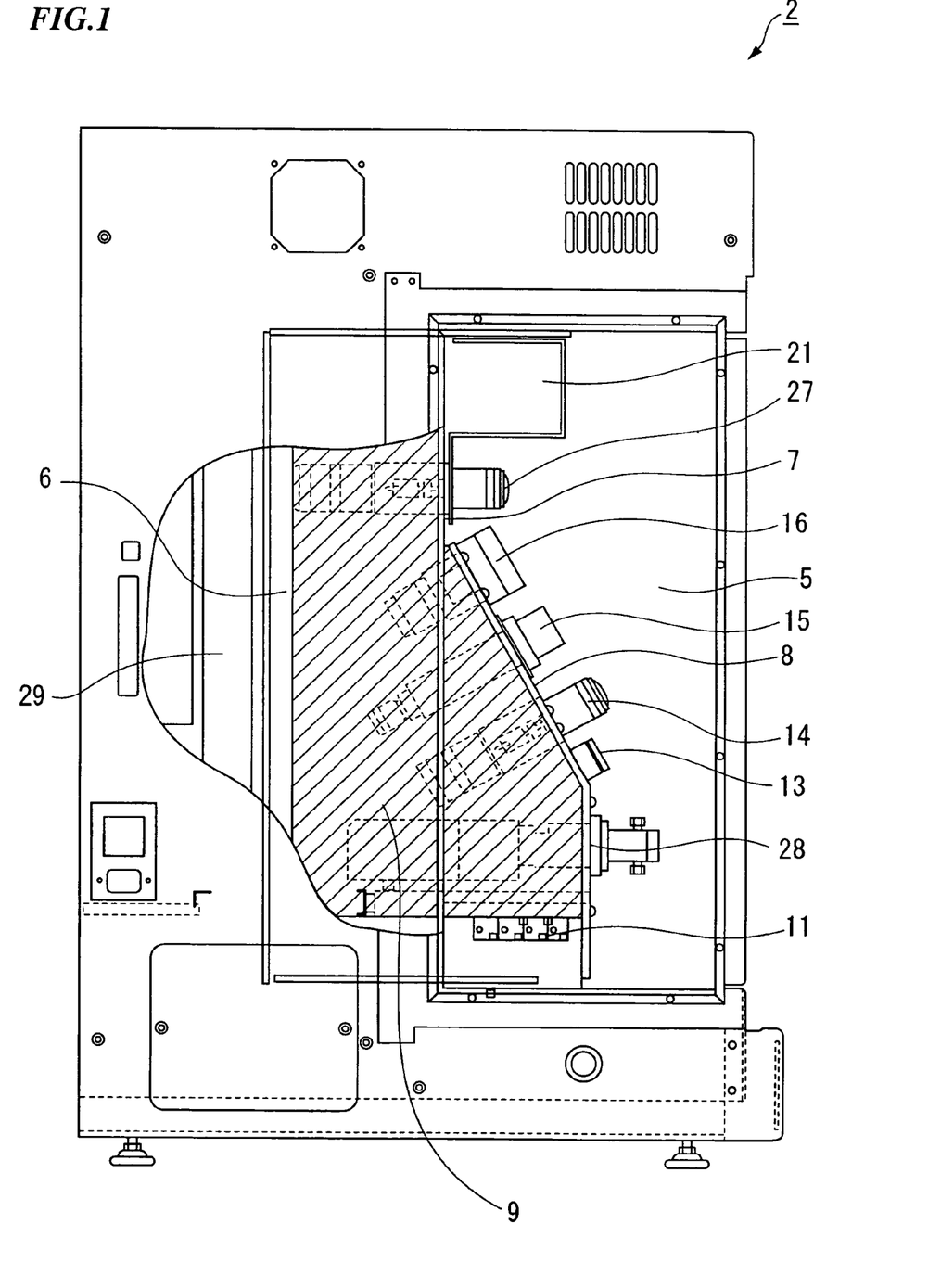
FIG. 1 is a side sectional view of the first unit according to one embodiment of the present invention.
Figure 2:
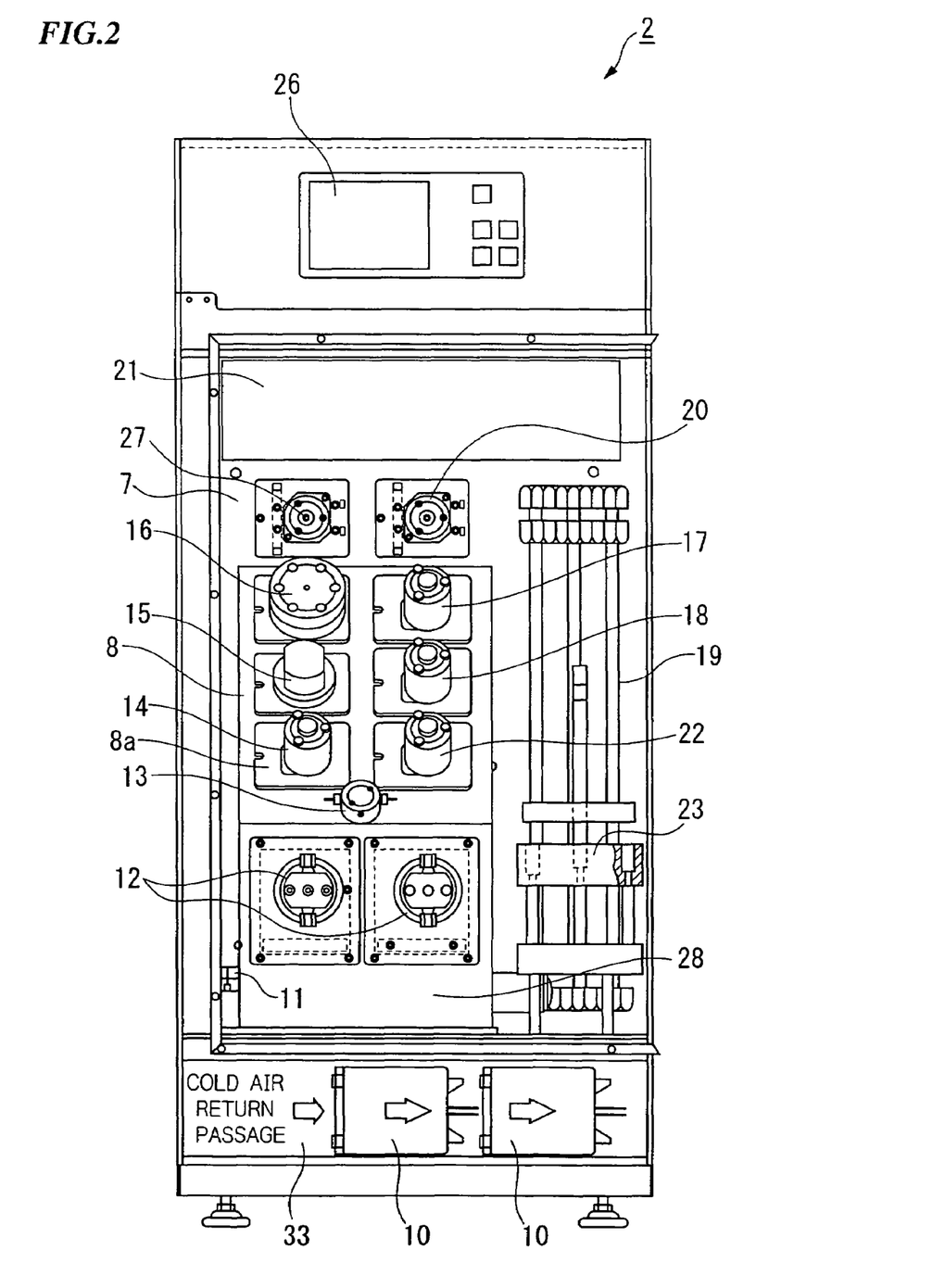
FIG. 2 is a longitudinal sectional view of the first unit according to one embodiment of the present invention.

FIG. 1 shows the side sectional view of the first unit, and FIG. 2 shows the longitudinal sectional view of the first unit.

As shown in FIG. 1, the inside of the first unit 2 is divided into the cooled portion 5 in the first unit 2 and the non-cooled portion 6 at the rear portion of the first unit 2 by a division plate 7 and thermal insulations 9 on the back part of the division plate 7. The attached panel 28 in which the upper portion thereof is inclined toward the division plate 7 is installed in the cooled portion 5 ahead the division plate 7. As shown in FIG. 2, the liquid feed pumps 12 are arranged at the perpendicular portion which is the front surface of the attached panel 28, and a branch block 13, a bidirectional valve 14, a damper 15, a mixer 16, an injection valve 17, and hexa-directional valves 18 and 22, are arranged at the front surface of the inclined portion 8 of the attached panel 28, respectively. Moreover, the hexa-directional valves 20, 27 and the detector 21 are installed above the attached panel 28 in the cooled portion 5, and the separation column 19 and a simple fraction collector 23 are installed at the side of the attached panel 28.

In the present embodiment, by arranging the liquid feed pumps 12, the branch block 13, the bidirectional valve 14, the damper 15, the mixer 16, the injection valve 17, while the hexa-directional valves 18 and 22 on the attached panel 28, the worker is able to perform operations simply. Moreover, in the present embodiment, by making the upper portion of the attached panel 28 the inclined portion 8, the area of the attached panel 28 can be extended in a limited space that is in the cooled portion 5 at the inside of the first unit 2. In addition, by making the upper portion of the attached panel 28 the inclined portion 8, there is also an advantage that cold air easily flows around each apparatus arranged on an inclined portion 8. Moreover, by such an inclination, it is also advantageous that the maintenance such as replacement, repair or the like of the each apparatus installed on the inclined portion 8 becomes easy.

The electrical parts 29 such as electrical circuits, the substrate, the power supply, and the like constituting the liquid feed pumps 12, the bidirectional valve 14, the damper 15, the mixer 16, the injection valve 17, and the hexa-directional valves 18, 20, 22, 27 are disposed in the non-cooled portion 6 of the rear part of the first unit 2. Moreover, the light source, the lens, and the light receiving portion of the detector 21 are also disposed in the non-cooled portion 6 of the rear part of the first unit 2. Therefore, condensation on the electrical parts 29 can be prevented, and failure of the electrical system is not likely to occur. In addition, by insulating the electrical parts 29 thermally from the cold, it is possible for the heat generated from the electrical parts 29 not to be transmitted to the cooled portion 5.

A console panel 26 is attached to the front surface of the upper portion of the outer surface of the first unit 2, and by using the console panel 26, the setting of a parameter and the monitoring can be performed. On the other hand, the lowest portion of the first unit 2 serves as the cold air duct 33, and a bottom plate 39 having a plurality of vent holes 39a is provided between the cooled portion 5 in the first unit 2 and the cold air duct 33 in the lowest portion of the first unit 2 (See FIG. 5). Moreover, the deaeration chambers 10 for removing dissolved gas in the eluent and/or the sample are installed in the cold air duct 33.

In the present embodiment, by providing the deaeration chambers 10 in the cold air duct 33, the eluent and/or the sample can be cooled using surplus cold energy.

Figure 3:
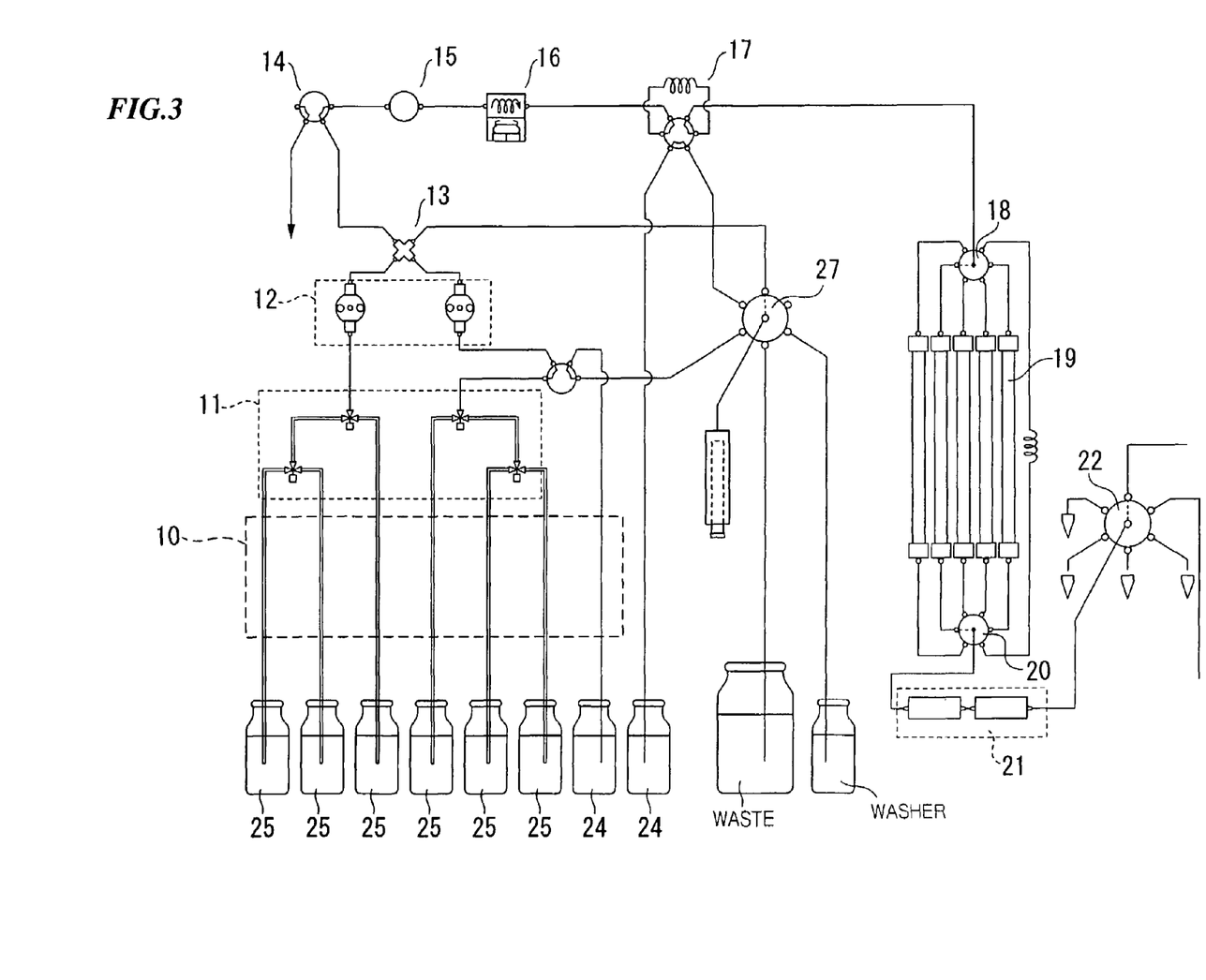
FIG. 3 is a channel view of the liquid chromatography apparatus according to one embodiment of the present invention.

Next, the action of the liquid chromatography apparatus will be explained while referring to the channel view of the liquid chromatography apparatus in FIG. 3.

First, eluent 25 is fed to the liquid feeding pumps 12, and passes tri-directional valve 11 installed at the side surface of the attached panel 28. Then, dissolved gas in eluent 25 is removed by the deaeration chambers 10, and eluent 25 is cooled while passing the deaeration chambers 10. Afterward, the pulse in eluent 25 is damped in the damper 15, via the branch block 13 and the bidirectional valve 14 by the liquid feeding pump 12. Then, eluent 25 is mixed by the mixer 16 and is fed to the injection valve 17.

On the other hand, dissolved gas in sample 24 is removed by the deaeration chambers 10. Furthermore, sample 24 is cooled while passing the deaeration chambers 10, then is fed into the injection valve 17.

Sample 24 is added to eluent 25 in the injection valve 17, and is injected into the separation column 19 via the hex-directional valve 18. Thereafter, sample 24 is separated into each component in the separation column 19, then each component is detected by the detector 21 via the hexdirectional valve 20. Then, each component is fed to the fraction collector 23 via the hexdirectional valve 22.

In addition, though sample 24 and eluent 25 are outside of the first unit 2 for compactifing the first unit 2, both sample 24 and eluent 25 are fully cooled while passing through the inside of the deaeration chambers 10.

Figure 4:
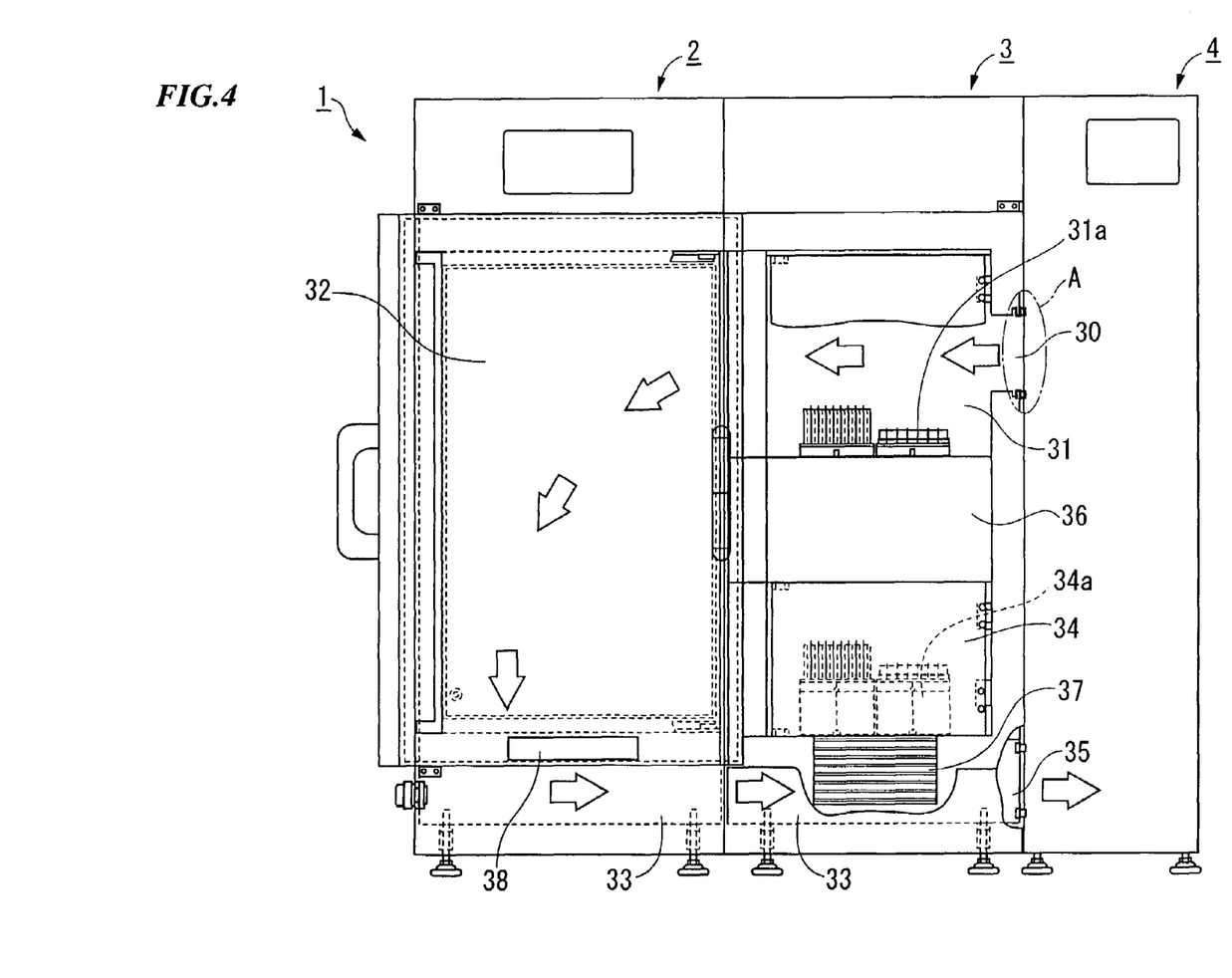
FIG. 4 is a longitudinal sectional view showing an example of one embodiment of the liquid chromatography apparatus consisting of a first unit, a second unit and a cooling apparatus according to one embodiment of the present invention.
Figure 5:
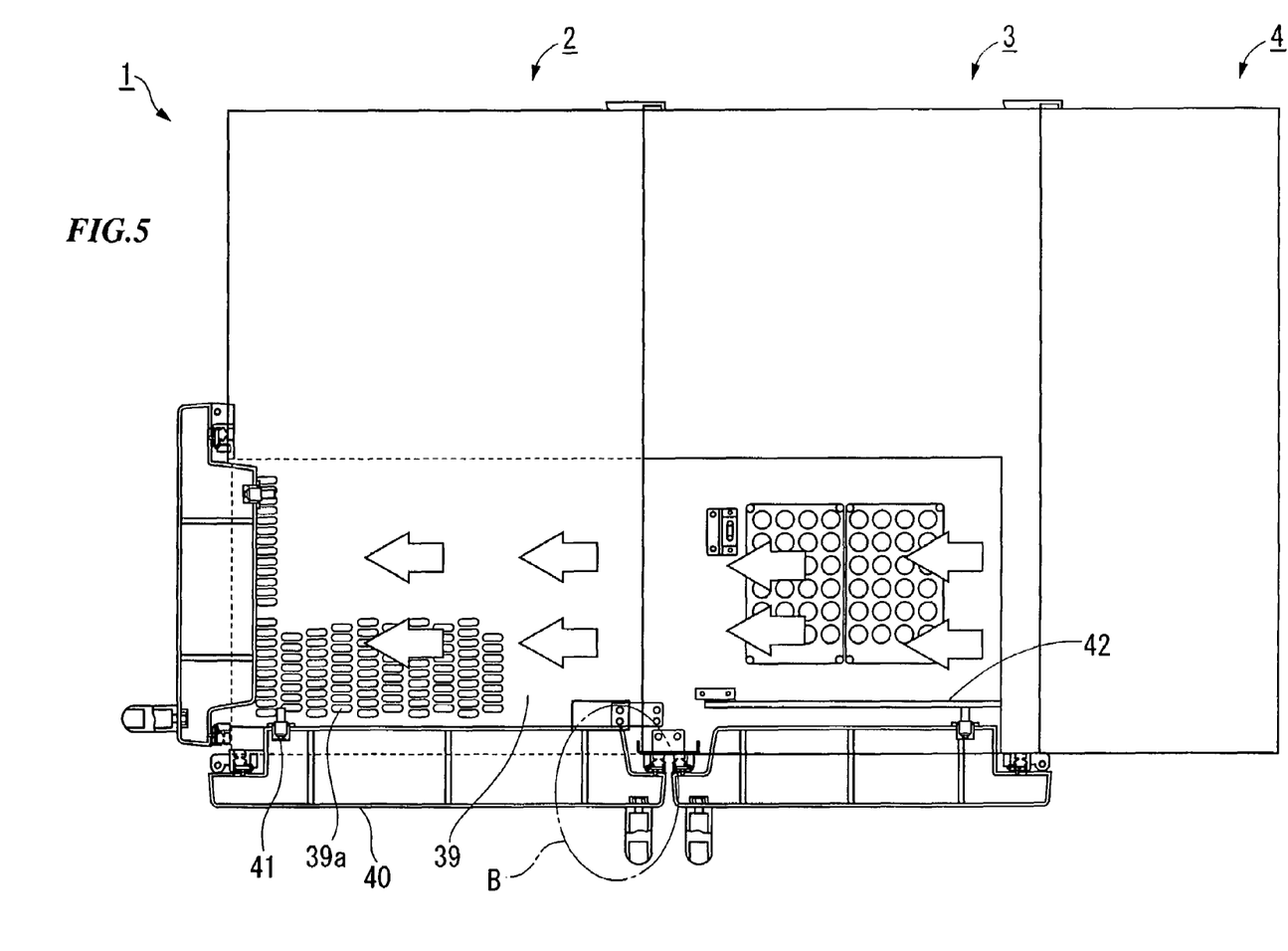
FIG. 5 is a plane sectional view showing an example of one embodiment of the liquid chromatography apparatus consisting of a first unit, a second unit and a cooling apparatus according to one embodiment of the present invention.

FIG. 4 is the longitudinal sectional view showing an example of one embodiment of the liquid chromatography apparatus consisting of the first unit, the second unit and the cooling apparatus, and FIG. 5 is the plane sectional view thereof.

As shown in FIG. 4, in the liquid chromatography apparatus 1 according to the present embodiment, the first unit 2, the second unit 3, and the cooling apparatus 4 are connected, and are attached to or removed from each other.

In the liquid chromatography apparatus 1 according to the present embodiment, by unitizing the first unit 2, the second unit 3, and the cooling apparatus 4, respectively, and being able to be attached to or removed from each other, a optimal combination of the apparatus can be chosen for every experiment.

The second unit 3 is a unit for preserving the sample before and after analysis, and the inside thereof is divided into upper portion 31 and lower portion 34 by the division portion 36. The upper portion 31 of the second unit 3 is used as an installation place of the sample 31a, and the lower portion 34 thereof is used as an installation place of the fractionated solution 34a, respectively.

The lowest portion of the second unit 3 serves as the cold air duct 33, and the heat sink 37 for cooling the lower portion 34 in the second unit 3 by surplus energy may be installed.

In a connecting portion between the first unit 2 and the second unit 3, an opening portion (not shown in the drawings) for passing the cold air is formed. On the other hand, in the connecting portion between the second unit 3 and the cooling apparatus 4, while an opening portion for the cold air flow out opening 30 of the cooling apparatus 4 is formed at the side of the upper portion 31 in the second unit 3, one end of the cold air duct 33 at the lowest portion of the second unit 3 was connected to the cold air return opening 35 formed in the cooling apparatus 4. Moreover, at the circumference of the opening portion which is formed in the connecting portion between the first unit 2 and the second unit 3, the packing is attached for preventing the gap from being formed at the connecting portion. At the circumference of the opening portion which is formed in the connecting portion between the second unit 3 and the cooling apparatus 4, the packing is attached for preventing the gap from being formed at the connecting portion.

As shown in FIG. 5, in the first unit 2 and the second unit 3, the first doors 40 of the hollow structure are provided to improve the heat insulation, respectively. In the hollow structure of the first door 40, the check valves 41 are attached for preventing outside air from flowing into the hollow structure of the first door 40. Thereby, the hollow portion of the first door 40 can be maintained at a lower pressure condition than the outside air to improve the heat insulation.

Moreover, the drying agents 38 are enclosed in the hollow portion of the first door 40, and thereby condensation in the hollow portion can be prevented.

In addition, in the second unit 3, the second door 42 are provided at the upper portion 31 and the lower portion 34 at the inside of the first door 40, respectively.

Next, the cold air route at the inside of the first unit 2 and the second unit 3 will be explained while referring to FIGS. 4 and 5.

The cold air which flows out from the cold air flow out opening 30 formed in the cooling apparatus 4 flows into the cooled portion 32 in the first unit 2 via the upper portion 31 in the second unit 3. Then, the cold air which flowed into the cooled portion 32 in the first unit 2 flows into the cool air duct 33 provided at the lowest portion of the first unit 2 via a plurality of vent holes 39a formed in the bottom plate 39 of the cooled portion 32. Thereafter, the cold air which flowed into the cold air duct 33 provided at the lowest portion of the first unit 2 returns the cooing apparatus 4 through the cold air returning opening 35 via the cold air duct 33 provided at the lowest portion of the second unit 3 as depicted by the arrows in FIG. 4.

In the liquid chromatography apparatus 1 according to the present embodiment, by forming the cold air flow out opening 30 of the cooling apparatus 4 at the side surface of the upper portion 31 in the second unit 3, the sample 31a put on the upper portion 31 in the second unit 3 can be maintained at a low temperature, while by not entering the cold air in the lower portion 34 of the second unit 3, a evaporation of the fractionated solution 34a put on the lower portion 34 in the second unit 3 can be prevented.

In addition, in the present embodiment, the fractionated solution 34a can be cooled through the heat sink 37 in the cold air duct 33 provided at the lowest portion of the second unit 3.

The outside surfaces of the first unit 2 and the second unit 3, the inside surface of the cooled portion 32 in the first unit 2, and the inside surfaces of the upper portion 31 and the lower portion 34 in the second unit 3 are covered by resin.

Thereby, while condensation on the outside surfaces of the first unit 2 and the second unit 3 can be prevented, the effusion of the cold energy from the cooled portion 32 in the first unit 2 and from the inside surfaces of the upper portion 31 and the lower portion 34 in the second unit 2 can be prevented.

Figure 6:
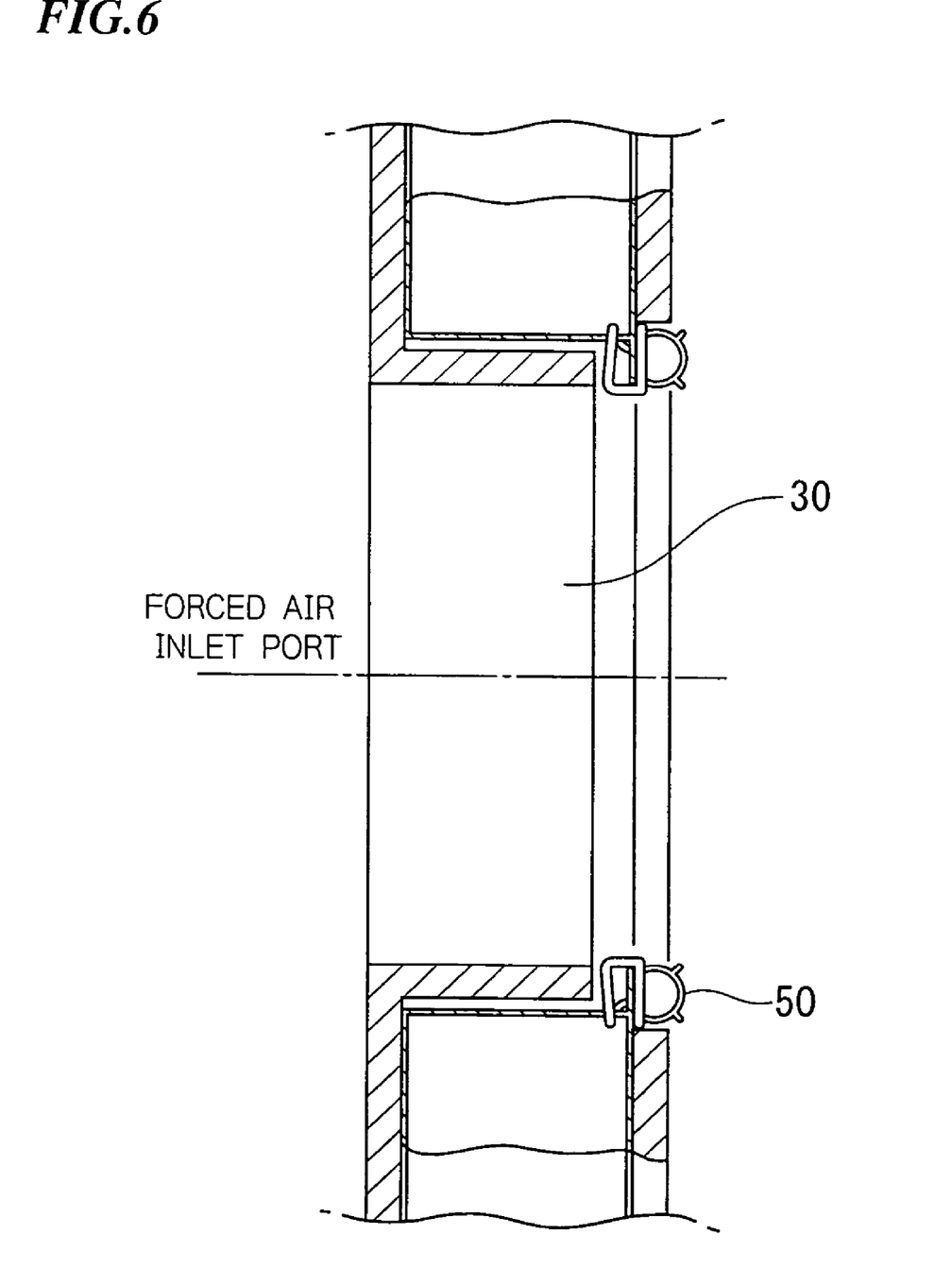
FIG. 6 is a cross-sectional detail view of an opening portion formed at a side surface of the upper portion in the second unit according to one embodiment of the present invention.

FIG. 6 shows the cross-sectional detail of the opening portion as the cold air flow out opening 30 formed at the side of the upper portion 31 in the second unit 3 to communicate with the cooling apparatus 4. The air enclosing packing 50 is attached to the circumference of the opening portion which are formed at the side of the upper portion 31 in the second unit 3. Although not shown in figures, the circumference of the cold air returning opening 35 and the connecting portion of the cool air ducts 33 of the first unit 2 and the second unit 3 have similar sealing structures. Thereby, while the unit connecting portion can be tightly sealed, the effusion of the cold energy to the circumference can be prevented.

Figure 7:
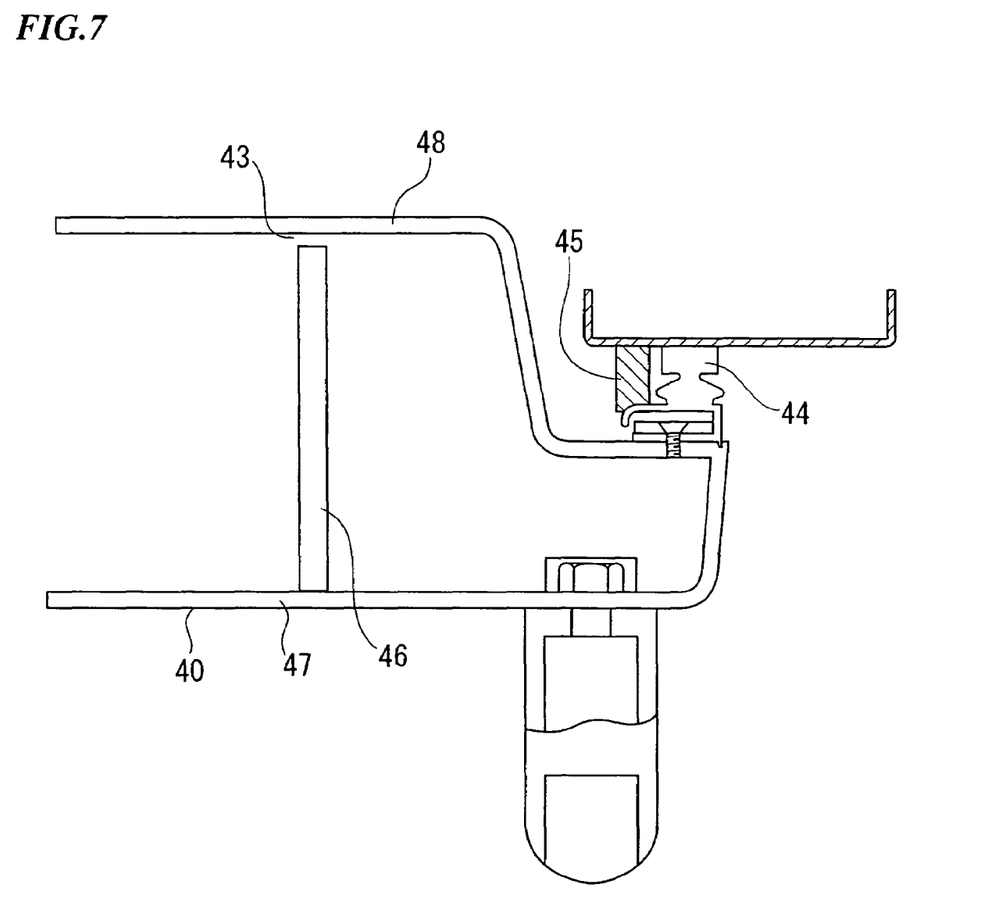
FIG. 7 is a cross-sectional detail view of the first door according to one embodiment of the present invention.

FIG. 7 shows the cross-sectional detail of the first door 40.

The packing with magnet 44 is attached to the entire circumference at the inside of the first door 40, and thereby a sealing can be sufficiently performed around the entire circumference at the inside of the first door 40.

Furthermore, a second packing 45 is attached at the inside of the packing with magnet 44, thereby the heat insulation can be improved by forming a double sealing structure.

Moreover, in the hollow portion of the first door 40, the rib 46 is arranged between the outside face plate 47 and the inside face plate 48 constituting the first door 40, thereby it is prevented that the first door 40 is deformed by atmospheric pressure. In this case, the rib 46 is attached to the outside face plate 47 alone to form the gap 43 between the rib 46 and the inside face plate 48, and thereby it can be prevented that the rib 46 becomes a heat bridge.

While preferred embodiments of the present invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims. For example, in the above-mentioned embodiment, the first unit 2, the second unit 3, and the cooling apparatus 4 are connected. However, in the present invention, only the first unit 2 and the cooling apparatus 4 may be connected, while a case in which it is not necessary to cool, only the cooling apparatus 4 may be removed.

Moreover, in the above-mentioned embodiment, while the sample 24 installed on the first unit 2 is used, each separated component of the sample 24 is fed to the simple fraction collector 23 in the first unit 2. However, in the present invention, when the sample 31a put on the upper portion 31 in the second unit 3 is injected into the separation column 19, and the fraction collector is put on the lower portion 34 in the second unit 3, then each separated component may be fed to the fraction collector.

What is claimed is:

1. A liquid chromatography apparatus comprising a separation column, a liquid feed pump which feeds eluent into the separation column, a detector which detects elution component fed from the separation column, and a plurality of valves which control a flow of liquid which passes from the liquid feed pump to the detector via the separation column, wherein the liquid feed pump, the separation column, the detector, and the plurality of valves are disposed in a cooled portion within a first unit, and among the mechanical parts and the electrical parts that respectively form the liquid feed pump, the detector, and the plurality of valves, the electrical parts are disposed in a non-cooled portion within the first unit.

2. A liquid chromatography apparatus comprising a separation column, a liquid feed pump which feeds eluent into the separation column, a detector which detects elution component fed from the separation column, and a plurality of valves which control a flow of liquid which passes from the liquid feed pump to the detector via the separation column, wherein at least one part of each of the liquid feed pump, the detector and the plurality of valves, as well as the separation column are disposed in a cooled portion formed at the inside of a first unit, and at least one of parts which require supply of electricity of the liquid feed pump, the detector and the plurality of valves is disposed in a non-cooled portion formed at the inside of the first unit.

3. A liquid chromatography apparatus according to claim 1 or 2, wherein the liquid feed pump and the plurality of valves are arranged on an attached panel fitted in the cooled portion at the inside of the first unit.

4. A liquid chromatography apparatus according to claim 3, at least one part of the attached panel where the liquid feed pump and the plurality of valves are arranged is inclined.

5. A liquid chromatography apparatus according to claim 1 or 2, comprising a first unit which has an opening portion on the side to allow the cold air to pass through, a second unit which has an opening portion on the side to allow the cold air to pass through, and inside thereof is divided into upper and lower portions to preserve the sample, and a cooling apparatus, wherein the first unit, the second unit, and the cooling apparatus are attached to or removed from each other.

6. A liquid chromatography apparatus according to claim 5, comprising a cold air route, in which, cold air which flows out from a cold air flow out opening formed in the cooling apparatus flows through the inside of the second unit and returns to a cold air return opening formed in the cooling apparatus, via the cooled portion of the inside of the first unit and cold air ducts provided at the first unit and the second unit.

7. A liquid chromatography apparatus according to claim 6, comprising a deaeration chamber which is provided in the cold air duct at the first unit for removing dissolved gas in the eluent and/or the sample.

8. A liquid chromatography apparatus according to claim 6, comprising a heat sink which is provided in the cold air duct at the second unit for cooling the inside of the second unit.

9. A liquid chromatography apparatus according to claim 5, comprising packings which are provided to the circumferences of the opening portions which are formed at the first unit and the second unit to allow the cold air to pass through.

10. A liquid chromatography apparatus according to claim 5, wherein first doors of a hollow structure are provided at the first unit and the second unit, respectively.

11. A liquid chromatography apparatus according to claim 10, wherein a rib for reinforcing the hollow portion of the first door is arranged on one face plate constituting the hollow portion, and a gap is formed between the rib and another face plate.

12. A liquid chromatography apparatus according to claim 10, wherein a drying agent is enclosed in the hollow portion of the first door.

13. A liquid chromatography apparatus according to claim 10, at the inside of the first door provided at the second unit, second doors to maintain the coolness are provided in an upper portion and a lower portion of the second unit, respectively.

14. A liquid chromatography apparatus according to claim 5, wherein first doors of a hollow structure are provided at the first unit and the second unit, respectively, and a check valve for preventing outside air from flowing into the hollow structure of the first door is provided at the first door.

* * * * *